United States Patent [19]

Borroff et al.

[11] Patent Number: 4,661,535

[45] Date of Patent: Apr. 28, 1987

[54] THERMOPLASTIC COMPOSITION

[75] Inventors: Michael J. Borroff, West Yorkshire; Donald A. Willstead, Hampshire, both of England

[73] Assignee: Johnson & Johnson, New Brunswick, N.J.

[21] Appl. No.: 753,217

[22] Filed: Jul. 9, 1985

[30] Foreign Application Priority Data

Jul. 13, 1984 [GB] United Kingdom ............... 8417872

[51] Int. Cl.$^4$ .......................... C08L 67/04; A61F 5/04
[52] U.S. Cl. .................................... 523/105; 523/513; 523/521; 523/522; 523/526; 525/92; 525/186; 525/415; 128/90
[58] Field of Search .............. 525/92, 186, 190, 415; 523/415, 513, 521, 522, 526, 105; 128/90

[56] References Cited

U.S. PATENT DOCUMENTS

| | | | |
|---|---|---|---|
| 3,637,544 | 1/1972 | Lundberg | 525/186 |
| 4,144,223 | 3/1979 | Kent | 525/186 |
| 4,240,415 | 12/1980 | Wartman | 528/359 |
| 4,274,983 | 6/1981 | Kent | 524/522 |

FOREIGN PATENT DOCUMENTS 2125803 3/1984 United Kingdom .

*Primary Examiner*—John C. Bleutge
*Assistant Examiner*—Patricia Short

[57] ABSTRACT

A thermoplastic composition, especially for use as an orthopedic splinting or casting material comprises a crosslinked polymeric component and a filler. The crosslinked polymeric component comprises a polycaprolactone, such as poly(epsilon)caprolactone, and a thermoplastic rubber in a ratio of from about 4:1 to about 1.5:1 by weight. Styrene-butadiene-styrene and styrene-isoprene-styrene triblock copolymers are particularly suitable thermoplastic rubbers.

Crosslinking may be carried out using an organic peroxide such as benzoyl peroxide. The filler is preferably a mixture of talc and silica.

15 Claims, No Drawings

THERMOPLASTIC COMPOSITION

This invention relates to thermoplastic compositions, especially for use as orthopaedic splinting and casting materials.

In many cases of injury or disease, it is desirable to immobilise or support the part of the body affected. A well known example is the use of immobilising casts to aid the healing of broken bones, but splints and casts are also used to immobilise inflamed or injured joints, and to support strained or sprained ligaments or muscle. Splints and casts are also used after orthopaedic surgery.

Traditionally, plaster of Paris has been used as a splinting and casting material in such cases. However, plastic splints and casts are heavy and cumbersome, slow to dry out, and are relatively easily damaged, especially by water. Moreover, they are only partly transparent to X-rays, so that it can be difficult to monitor the progress of bone injuries which are immobilised in plaster. Plaster splints have the additional disadvantage that progressive correction of the deformity is not possible without the construction of a fresh splint for each correction. The facility for progressive correction is especially desirable in the serial splinting of certain orthopaedic deformities.

In order to avoid these disadvantages, synthetic thermoplastic resins and compositions have been used as splinting and casting materials, but these are not without their problems. An article by R. G. S. Platts in Bio-engineering in Britain, British Health Care & Technology 1975, entitled "Orthotics—Today and Tomorrow" describes the early types of thermoplastic splinting and casting materials. These materials, such as polyvinyl chloride (tradename—Darvic), polypropylene (tradename—Vitralene), acrylonitrile (tradename—Flexidur), polyethylene (tradenames—Vitrathene, Ortholon, Subortholon) are classified as high temperature thermoplastics, as the materials possess melting points in excess of 140° C. This high melting point precludes the possibility of moulding these materials directly on the patient's skin as severe burns would result. These materials thus require the use of positive plaster casts of the affected part, to allow moulding and the use of large ovens for softening the sheets. The construction of positive plaster casts is a particularly laborious and time consuming process.

To overcome these problems and disadvantages, it is desirable in such a splinting or casting material that it can be softened by exposure to air or water at a suitable temperature (for example at 60° C.), while at the same time remaining manageable, so that it can be shaped directly on the patient's skin, to give accurate support to the part of the body which is to be immobilised. On cooling, the casting material should harden again, without any substantial change in shape. With large applications (for example, functional cast braces for the management of long bone fractures of the tibia, femur, humerus or forearm bones), where firm compression of the injured extremity is essential, it is important that the splinting or casting material is not too stretchy when in the softened state, or compression cannot be applied. It is also desirable in large applications to have a relatively long setting time to enable full and detailed moulding and shaping to be carried out, before the material hardens. It has proved remarkably difficult to obtain synthetic thermoplastic splinting and casting materials which have these properties.

British Patent Specification No. 1366091 discloses synthetic resin casting materials based on cyclic ester polymers, and especially poly(epsilon)caprolactone. Polycaprolactone of suitable molecular weight has a convenient melting point of about 60° C., but above this temperature the polymer melt is a very soft tenaciously adhesive, mobile semi-fluid which is very difficult to control during handling and cutting. The additional of a filler gives more body to the polymer melt and reduces its adhesiveness, but the resulting blend tends to be inflexible and may crack when bent through a large angle.

A leaflet published by Interox Chemicals Ltd., (Luton, Bedfordshire, England) proposes crosslinking polycaprolactones by the addition of 1 to 10% organic peroxide. The resulting crosslinked polymers are suggested for use as heat-shrink materials, adhesives and in "orthopaedic applications". However, the products are also said to show an elastic memory which is highly undesirable in a splinting and casting material, as detailed moulding is only possible just as the material finally hardens.

Crosslinked polycaprolactones are also disclosed in U.S. Pat. No. 4240415. In this case, the crosslinking is effected by electron bombardment of the polycaprolactone. Splinting and casting material manufactured in accordance with U.S. Pat. No. 4240415 is commercially available under the trade name Aquaplast. It has been suggested that this material has a number of disadvantages, including some elastic memory, too much stretch when molten, and too short a setting time.

An alternative approach to rendering polycaprolactones more suitable for use as a splinting and casting material is disclosed in British Patent Specification No. 2015004 A. This specification teaches thermoplastic compositions comprising from substantially 70 to substantially 80 parts by weight of a poly(epsilon)caprolactone, from substantially 5 to substantially 20 parts by weight of a predominantly cis-1,4 polydiolefin and from 0 to substantially 10 parts by weight of an ionomer, the total of such polymeric materials being 100 parts by weight, and as filler from substantially 10 to substantially 30 parts by weight, per 100 parts by weight of polymeric material, of a silica or calcium silicate.

A composition in accordance with GB 2015004 A is also available commercially, under the trade name San Splint XR. It has been suggested that this composition is too stretchable.

We have now devised a thrermoplastic splinting and casting composition which has a desirably long setting time, and which has a low degree of stretch in the molten state. Moreover, the composition does not display any significant elastic memory, adhesion between layers of the material is good, and it has an improved flexural modulus and flexural strength as compared with other commercially available splinting and casting materials.

According to the present invention, there is provided a thermoplastic composition having a polymeric component comprising a crosslinked mixture of a polycaprolactone and a thermoplastic rubber, together with a filler, the polycaprolactone and thermoplastic rubber being present in the composition prior to crosslinking in a ratio of from about 4:1 to about 1.5:1.

Preferably, the polycaprolactone is a poly(epsilon)caprolactone. The weight average molecular weight of the polycaprolactone used will usually be at least 10,000 and more preferably at least 25,000, for example 45,000. Suitable polycaprolactones are available under the trade names PCL 700 (Union Carbide Corporation) and CAPA 601M (Laporte).

The thermoplastic rubber should preferably have a relatively low softening point, for example below 100° C. Styrene-butadiene-styrene and styrene-isoprene-styrene triblock copolymers are particularly suitable for use in the compositions of the present invention, but other thermoplastic rubbers having a suitably low softening point may also be used. Such other thermoplastic rubbers include ethylene-propylene-diene rubbers such as Vistalon 3708 (Essco Chemicals) and Dutral 535E (Motedison).

Trans-1,4-polyisoprene is a further example of a thermoplastic rubber which is suitable for use in compositions according to the present invention.

Examples of commercially available styrene-isoprene-styrene and styrene-butadiene-styrene triblock copolymers are Cariflex TR1107 and Cariflex TR1102 (Shell Chemicals) respectively. Of these two Cariflex rubbers, Cariflex TR1107 is preferred because it yields splinting and casting compositions having a longer setting time.

The proportion of polycaprolactone to thermoplastic rubber is from about 4:1 to 1.5:1. If this ratio is higher than 4:1, the composition is rather stiff and difficult to process, and rather soft in the molten state. At a ratio below 1.5:1, the composition has reduced adhesion and a shorter setting time. It is particularly preferred that the ratio of polycaprolactone to thermoplastic rubber is from 2.5:1 to 1.5:1 by weight, for example 2:1 by weight.

The ratio of polymeric component to filler may conveniently be varied from about 5:1 to 1:1. At a ratio above 5:1, the composition is more difficult to process due to its stickiness, and at a ratio below 1:1, the stiffness is somewhat too high, and the material has relatively poor resistance to stress cracking.

Preferably, the ratio of polymeric component to filler is from 3:1 to 2:1, for example 2.5:1.

Crosslinking of the polycaprolactone and the thermoplastic rubber can be achieved by a variety of methods, such as by means of ionising radiations or by means of chemical free-radical generators. Organic peroxides are the preferred free-radical generators, andd benzoylperoxide is particularly preferred. The organic peroxide may be added to the composition as a mixture with a plasticiser such as phthalate plasticiser.

In the compositions of the present invention, it is generally desirable to crosslink the polycaprolactone and the thermoplastic rubber to a lower degree than that hitherto proposed for polycaprolactone alone. When an organic peroxide such as benzoylperoxide is used, it is preferably used in an amount from 0.1% by weight to 1% by weight of the polymeric component, and more preferably from 0.1% to 0.6% by weight. If less than 0.1% by weight is used, very little crosslinking effect is observed, whereas if more than 0.6% by weight is used there is a tendency for the polycaprolactone/-thermoplastic rubber mixture to become too rubbery, leading to elastic memory effects, and poor moldability.

When benzoylperoxide is used as the crosslinking agent, the crosslinking reaction is preferably carried out at elevated temperature for a period between 1 minute and an hour. Particularly preferred conditions are a temperature of from 110° to 120° C. for a period of from 5 to 15 minutes, e.g. 10 minutes.

The filler is used in the composition of the present invention mainly to reduce the tackiness of the melt during processing. It also serves to retain some heat, thereby extending the setting time. Talc is a particularly good filler which controls the tackiness of the polycaprolactone melt, but it does tend to reduce adhesion in the finished splinting and casting material. In order to avoid this, the filler preferably consists of or includes a silica or calcium silicate, which improves the adhesion of the finished splinting material. Some improvement in the flexural modulus and flexural strength is also observed, since silica has some reinforcing properties.

Preferably, the filler includes some talc and some silica, for example a 1:1 mixture of talc and silica by weight.

If silica is used as a filler, it preferably has a particle size less than 50 nm, and more preferably less than 25 nm. A particularly suitable form of silica is available under the trade name Aerosil 130V. Aerosil 130V is a fumed silica which has a particle size of approximately 16 nm. It will be appreciated, of course, that other silica fillers, such as clay or powdered slate, could also be used. Similarly, other inorganic fillers, such as calcium carbonate, could be used in place of the talc.

The composition of the present invention may if desired be rendered opaque or coloured by the addition of one or more pigments. For example, the composition may contain titanium dioxide. The amount of pigment added will usually be from 0.1 to 10% by weight of the composition, and preferably from 1 to 8% by weight, e.g. 4% by weight. It will be appreciated that more than 10% by weight can be added if desired, but it will usually then be necessary to reduce the amount of filler used by a corresponding amount.

A minor amount (e.g. less than 1% by weight) of an antioxidant such as a hindered phenol antioxidant, may also be incorporated in the composition of the invention. A suitable antioxidant is ICI's CP antioxidant. The antioxidant is preferably added after the crosslinking stage to avoid inhibition of the peroxide free radical reaction.

The various components of the composition according to the invention may be blended in any order, but the antioxidant is preferably added last after crosslinking has taken place. For example, the filler may be blended with the polymeric component either before or after the polymeric component has been crosslinked. For ease of mixing, however, it is preferred that the filler be blended with the polymeric component prior to crosslinking the latter. A particularly advantageous procedure is to blend the polycaprolactone and the thermoplastic rubber at about 80° C. with approximately half of the fillers and pigment in an internal mixer or 2-roll mill. When this mix is blended, the remainder of the filler is added. When this is well mixed, the peroxide is added and the temperature raised for crosslinking to take place.

A thermoplastic composition according to the present invention is now described by way of illustration, in the following Examples.

EXAMPLE 1

A mixture of the following ingredients was compounded together using a 2-roll mill, in two stages as described above:

| | Parts by weight |
|---|---|
| LaporteCAPA 601M polycaprolactone | 1000 |
| Shell Cariflex TR1107 styrene-isoprene-styrene triblock copolymer | 500 |
| Italian 00000 talc | 250 |
| Aerosil 130V fumed silica | 250 |
| Titanium dioxide ADM | 80 |
| Interox BP 50 FT benzoylperoxide (50% w/w with phthalate plasticiser) | 7.5 |

Crosslinking of the polymeric components was completed by maintaining the blend at 110°–120° C. for 10 minutes. The resulting composition had a melting point of 58° C. and was well suited for use as splinting and casting material.

The composition of the above Example was compared with a similar composition containing no benzoylperoxide, and with commercially available casting compositions, by means of standard methods for determining hardness, flexural modulus, flexural strength and overlap cohesion. The results are shown in the Table.

It will be seen that the composition according to the invention compares favourably with the commercially available splinting and casting materials in respect of setting time, flexural modulus and overlap cohesion. A significant increase in setting time is seen to be obtained by means of the crosslinking reaction. The flexural strength of the composition according to the invention is also seen to be considerably greater than any of the other materials tested.

EXAMPLE 2

Example 1 was repeated with the following mixture of components:

| | Parts by Weight |
|---|---|
| Union Carbide PCL 700 polycaprolactone | 1000 |
| Shell Cariflex TR1102 styrene-butadiene-styrene triblock copolymer | 500 |
| Italian 00000 talc | 500 |
| Titanium Dioxide ADM | 80 |
| Interox BP 50 FT benzoyl peroxide (50% w/w with phthalate plasticiser) | 9 |

The composition obtained was compared in physical properties with a similar composition to which no benzoyl peroxide was added, and the result are set out in Table 2. As can be seen, the inclusion of benzoyl peroxide in the composition of the invention results in increased setting time, without adversely affecting (and in some cases even improving) other physical properties of the composition.

EXAMPLE 3

Example 1 was repeated with the following mixture of components:

| | Parts by Weight |
|---|---|
| Union Carbide PLC700 polycaprolactone | 1000 |
| Esso Chemical Vistalon 3708 ethylene-propylene-diene terpolymer | 500 |
| Italian 00000 talc | 500 |
| Titanium Dioxide ADM | 80 |
| Interox BP 50 FT benzoyl peroxide (50% w/w with phthalate plasticiser) | 4.3 |

Again, the physical properties of the resulting composition were compared with a similar composition which had not been crosslinked (see Table 2). The composition according to the invention is seen to be improved in setting time and other physical properties, as compared with the non-crosslinked composition.

TABLE 1

| Property | Composition According to The Example | Similar Composition Excluding Benzoyl Peroxide | ORTHOPLAST Splinting Material | Polyflex II | Aquaplast (US 4240415) |
|---|---|---|---|---|---|
| Initial Hardness (Molten) Shore 'A' | 43 | 45 | 30 | 43 | 45 |
| Setting Time to: | | | | | |
| Shore 'A' = 70 (min) | 3.15 | 2.95 | 4.55 | 4.30 | 2.95 |
| Shore 'A' = 95 (min) | 8.00 | 5.50 | 7.35 | 7.00 | 5.35 |
| Final Hardness Shore 'A' | 97 | 97 | 99 | 97 | 99 |
| Apparent Modulus of Elasticity (kg/cm$^2$)* | 5257 | 6100 | 4980 | 3683 | 3409 |
| Flexural Stress at Conventional Deflection (kg/cm$^2$)* | 103 | 86 | 77 | 59 | 55 |
| Overlap Cohesion (kg/cm$^2$) | 19.5 | 25.97 | 23.4 | 7.1 | 36.2 |

*B.S. 2782 Part 3 Method 335A 1978

TABLE 2

| | EXAMPLE 2 | | EXAMPLE 3 | |
|---|---|---|---|---|
| Property | | Similar Composition Excluding Benzoyl Peroxide | | Similar Composition Excluding Benzoyl Peroxide |
| Initial Hardness (Molten) Shore 'A' | 40 | 31 | 40 | 40 |
| Setting Time to: | | | | |
| Shore 'A' = 70 (min) | 3.30 | 2.00 | 3.00 | 3.85 |

TABLE 2-continued

|  | EXAMPLE 2 | | EXAMPLE 3 | |
|---|---|---|---|---|
| Property | | Similar Composition Excluding Benzoyl Peroxide | | Similar Composition Excluding Benzoyl Peroxide |
| Shore 'A' = 95 (min) | 8.00 | 5.50 | 6.50 | 5.50 |
| Final Hardness Shore 'A' | 99 | 97 | 98 | 98 |
| Apparent Modulus of Elasticity (kg/cm$^2$)* | 6600 | 5920 | 5610 | 4520 |
| Flexural Stress at Conventional Deflection (kg/cm$^2$)* | 88 | 67 | 62 | 76 |
| Overlap Cohesion (kg/cm$^2$) | 10.1 | 15.0 | 22.3 | 9.8 |

*B.S. 2782 Part 3 Method 335A 1978

We claim:

1. An orthopedic cast or splint comprising a mixture of a polycaprolactone and a thermoplastic rubber, crosslinked with from 0.1 to 1.0 percent of an organic peroxide together with a filler, the polycaprolactone and thermoplastic rubber being present in the composition prior to crosslinking in a ratio of from about 4:1 to about 1.5:1.

2. An orthopedic cast or splint according to claim 1 wherein the ratio of polycaprolactone to thermoplastic rubber prior to crosslinking is from 2.5:1 to 1.5:1 by weight.

3. An orthopedic cast or splint according to claim 1 wherein the polycaprolactone is a poly(epsilon)caprolactone.

4. An orthopedic cast or splint according to claim 1 wherein the polycaprolactone has a weight average molecular weight of at least 10,000.

5. An orthopedic cast or splint according to claim 4 wherein the weight average molecular weight of the polycaprolactone is at least 25,000.

6. An orthopedic cast or splint according to claim 1 wherein the thermoplastic rubber has a softening point below 100° C.

7. An orthopedic cast or splint according to claim 6 wherein the thermoplastic rubber is selected from the group consisting of styrene-butadiene-styrene triblock copolymers, styrene-isoprene-styrene triblock copolymers, ethylene-propylene-diene polymers and trans-1,4 polyisoprene polymers.

8. An orthopedic cast or splint according to claim 1 wherein the ratio of polymeric component to filler is from about 5:1 to 1:1.

9. An orthopedic cast or splint according to claim 8 wherein the ratio of polymeric component to filler is from 3:1 to 2:1.

10. An orthopedic cast or splint according to claim 1 wherein said organic peroxide is benzoyl peroxide.

11. An orthopedic cast or splint according to claim 10 wherein said benzoyl peroxide is used in an amount from 0.1% to 0.6% by weight of the polymeric component.

12. A composition according to claim 1 wherein the filler is a mixture of talc, and calcium silicate.

13. An orthopedic cast or splint according to claim 12 wherein the filler is a mixture of talc and fumed silica having a particle size less than 50 nm.

14. An orthopedic cast or splint according to claim 1 further comprising one or more pigments in an amount from 0.1% to 10% by weight of the composition.

15. An orthopedic cast or splint according to claim 1 further comprising a hindered phenol antioxidant in an amount less than 1% by weight of the composition.

* * * * *